United States Patent [19]

Lampert

[11] 4,337,391

[45] Jun. 29, 1982

[54] MEASURING DEVICE

[76] Inventor: Shlomo I. Lampert, 10 Yemin Avot Str., Jerusalem, Israel

[21] Appl. No.: 104,769

[22] Filed: Dec. 18, 1979

Related U.S. Application Data

[63] Continuation of Ser. No. 589,403, Jun. 23, 1975, abandoned.

[30] Foreign Application Priority Data

Jul. 26, 1974 [IL] Israel .................................... 45350

[51] Int. Cl.³ ........................ G06C 27/00; G06G 1/02
[52] U.S. Cl. ................................ 235/70 A; 235/70 C; 235/71 A; 235/78 R
[58] Field of Search ............... 235/71 R, 71 A, 88 R, 235/86, 51 R, 116 R, 69, 89 R, 70 A, 78 R–78 RC; 116/135, 321, 335; 40/514, 518, 524; 35/9 R, 21, 24 B, 24 R, 24 C, 76

[56] References Cited

U.S. PATENT DOCUMENTS

| | | | |
|---|---|---|---|
| 842,495 | 1/1907 | Rose .................................... | 116/135 |
| 923,937 | 6/1909 | Bernst .................................. | 116/135 |
| 1,711,981 | 5/1929 | Andres et al. ....................... | 35/24 B |
| 2,146,005 | 2/1939 | Bernholz et al. ................... | 116/135 |
| 2,392,877 | 1/1946 | Pym ..................................... | 235/84 |
| 2,488,338 | 11/1949 | Senegas .............................. | 116/135 |
| 3,045,908 | 7/1962 | Donovan ............................ | 235/70 R |
| 3,139,854 | 7/1964 | Hedges et al. ...................... | 116/135 |
| 3,188,998 | 6/1965 | Wood .................................. | 116/135 |
| 3,905,547 | 9/1975 | Cyre et al. .......................... | 235/88 G |

FOREIGN PATENT DOCUMENTS

| | | | |
|---|---|---|---|
| 354254 | 12/1920 | Fed. Rep. of Germany ........ | 235/78 |
| 1259355 | 3/1961 | France ............................... | 235/88 R |
| 76113 | 2/1949 | Norway .............................. | 235/78 |

OTHER PUBLICATIONS

Shlomo I. Lampert, "The Attitude Pollimeter: A New Attitude Scaling Device", Journal of Marketing Research, vol. XVI, (Nov. 1979), pp. 578-582.

*Primary Examiner*—L. T. Hix
*Assistant Examiner*—Benjamin R. Fuller
*Attorney, Agent, or Firm*—Browdy and Neimark

[57] ABSTRACT

A device is provided for measuring a subject's reaction to stimuli, i.e., to measure a subject's indication of attitude, opinion, judgement, preference, evaluation, feeling, intention, etc. when presented with a question, problem, fact, situation or other stimuli the subjective response to which is sought to be measured, said device comprising a first means having a defined viewing area and a colored means having at least one colored area adapted to be viewed in said viewing area wherein the extent of colored area viewable is variable and adapted to indicate the degree of a subject's reaction to a specific stimulus.

23 Claims, 7 Drawing Figures

MEASURING DEVICE

This is a continuation of application Ser. No. 589,403 filed June 23, 1975, now abandoned.

The present invention relates to a device for measuring a subject's reaction to stimuli. More specifically the present invention relates to a device adapted as an aid to a person engaged in research and polling especially in the social sciences.

In the social sciences like psychology, sociology, political science etc., there is a need to identify and/or measure properties of objects, events, states and/or people through the use of attributes and/or factors, and/or variables, e.g., $X_1, X_2, X_3$ ... etc., yielding categories, classes or values within each attribute, factor or variable, e.g., $A_1, A_2, A_3, \ldots$ etc.

The identification and/or the measurement of properties are aimed at producing correspondence between empirical elements and a formal model consisting of abstract elements, e.g., numbers, determining the relationship between these elements, and determining the operations which can be performed on them.

Four basic types of measurement scales are used in the social sciences. One such scale is the nominal scale in which it is possible to assign elements to categories $A_1$ or $A_2$ or $A_3$ ... etc., where by definition $A_1 \neq A_2 \neq A_3$ etc. and numerical values that may be assigned to them are of no meaning except for category identification, e.g., $A_1$=Male; $A_2$=Female. Mathematically, this scale represents permutation of groups of $y=f(x)$.

A second scale is the Ordinal Scale in which it is possible to assign elements to categories or classes $A_1$ or $A_2$ or $A_3$ ... etc., where the categories or classes establish a monotonic increasing function e.g. $A_1 < A_2 < A_3$, and within each category the units are considered as homogeneous, e.g., elementary education, high school education, college education. Any array of numbers that will maintain a monotonic increasing function is acceptable 1, 2, 4 etc., or 12, 29, 41 ... Mathematically, this scale yields isotonic group of $y=f(x)$, where $f(x)$ is any increasing monotonic function.

A third scale is the Interval Scale in which the elements are assigned along a defined continuum, e.g., like—dislike. Numbers can represent points on the continuum, where differences among people regarding the attribute, factor or variable are equal to the differences among the numbers (in any preselected units of measurements) i.e., if two subjects scored $A_1$ and $A_2$ respectively $(A_1-A_2)$ represents the difference between the values. This scale does not possess an absolute zero point, thus no ratios are allowed, like degrees in centigrade. Mathematically, this scale represents a general linear group $y=a+bx$, where $b>0$.

The fourth type of scale is the ratio scale in which the elements are assigned values, on a continuum where an absolute zero does exist, thus all arithmetic operations are permissible with these values. Thus, if two subjects score values of $A_1$ and $A_2$ respectively, taking the ratio of $(A_1/A_2)$ and vice versa, is allowed, like measurement of income height. Mathematically, similarity groups are defined through $y=cx$, where $c>0$.

Many other measurement techniques were developed where in all cases they represent modified forms of these basic scales.

Of great importance within the social sciences is the measurement of intervening variables, i.e., the variables which link the reality in which the individual exists with his subjective responses or behavior. Such intervening variables include motivations, perceptions, cognitions, attitudes, opinions, judgements, preferences, evaluations, feelings, intentions, satisfactions etc. Since these variables are on the whole subjective, an absolute zero point does not exist in most of them. Thus, the ratio scale, for all practical purposes is of lesser value in measurements within the social sciences. For variables for which there is no theoretical constraints for the use of values on a continuum, but which do not have an absolute zero point, the most sophisticated scale analytically, and the one to which a large variety of statistical tools can be applied—is the interval scale. However, a large percentage of the general population find it difficult and, at times impossible, to place themselves in an interval scale for it is extremely difficult for people to express an opinion on a continuum as presented to them by present techniques wherein a subject must designate an arbitrary point between two poles as representing his position relative to the values represented by said poles. Rather, the ordinal scale seems to most people as a scale to which it is easier for them to relate, but the statistical analysis of such data is quite limited.

According to the present invention there has now been found a device which combines the desired statistical properties of the interval and ratio scales with the ease of measurement of the ordinal scale. Thus according to the present invention there is provided a device for measuring a subject's reaction to stimuli comprising a first means having a defined viewing area and a colored means having at least one colored area adapted to be viewed in said viewing area wherein the extent of colored area viewable is variable and adapted to indicate the degree of a subject's reaction to a specific stimulus.

The term "reaction to stimuli" as used herein is intended to connote the subject's indication of attitude, opinion, judgement, preference, evaluation, feeling, intention, etc. when presented with a question or, problem, the subjective response to which is sought to be measured.

The present invention also provides a method of measuring a subject's reaction to stimuli, as hereinbefore defined, comprising presenting a subject with a device comprising a first means having a viewing area and a colored means having at least one colored area adapted to be viewed in said viewing area wherein the extent of colored area viewable is variable; instructing the subject to vary the extent of colored area viewable with relation to said viewing area to indicate the degree of said subject's reaction to a specific stimuli; and noting the extent of colored area viewable as a result of the subject's action.

While the invention will now be described in connection with certain preferred embodiments, it will be understood that it is not intended to limit the invention to these particular embodiments. On the contrary, it is intended to cover all alternatives, modifications and equivalent arrangements as may be included within the scope of the invention as defined by the appended claims. Nevertheless it is believed that embodiments of the invention will be more fully understood from a consideration of the following illustrative description read in conjunction with the accompanying drawings, in which:

Figure 1:
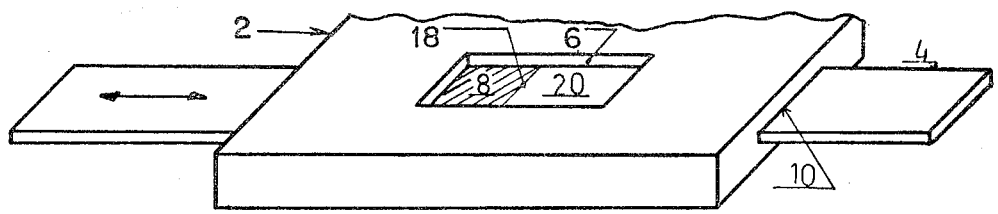
FIG. 1 is a perspective view of a device according to the present invention.

Referring now to FIG. 1 there is illustrated a device according to the present invention comprising as a first means a housing 2, as a colored means a member 4 adapted for reciprocal sliding movement in said housing and a viewing area 6 in said housing through which at least part of said sliding member is viewable wherein said sliding member comprises at least one colored area 8. The housing as shown is rectangular in shape having a slot 10 cut through its major axis and said member has a cross-section substantially the same as said slot and a length greater than said housing whereby said member is adapted for manipulation from both ends thereof.

As will readily be realized many variations of even this embodiment are possible. For example the housing could be square, or any other geometrical or non-geometrical shape and the sliding member could be shorter in length than the housing having manipulating members projecting from additional apertures cut in said housing for said purpose. The housing could also be a liquid-tight tubular housing of e.g. glass or plastic and the sliding member could comprise a piston arrangement adapted to reciprocally slide in said tube and to move a colored liquid in said tube wherein said liquid is immissible with and forms an interface with a second transparent or colored liquid.

Thus, it will be appreciated that the present invention provides a device for measuring a subject's reaction to stimuli as hereinbefore defined comprising a first means having a viewing area and a colored means having at least one colored area wherein said colored means and said viewing area are in movable relation to each other and whereby the positioning of said colored means with relation to said viewing area is adapted to indicate the degree of a subject's reaction to a specific stimulus.

A variation of the device according to the invention is one wherein the extent of colored area viewable is varied by further means in movable relation to said colored means said colored means being fixed with reference to the viewing area whereby the positioning of said further means with relation to said colored area is adapted to indicate the degree of a subject's reaction to a specific stimulus.

In practice a device according to said latter embodiment could comprise a housing having a defined viewing area and a colored area adapted to be viewed through said viewing area and having a sliding member adapted to override said colored area and be positioned with relation thereto in such a manner that all, none or part of said colored area is viewable through said viewing area. In said embodiment said sliding means could be associated with a scaled reference which translates the amount of colored area covered into numerical values as discussed hereinafter with reference to other embodiments.

Another device according to said latter embodiment could be in the simple form of two concentric discs wherein one disc is colored and the other is neutral or colored and both discs have a radial slit whereby the bottom disc is adapted by means of said slits to be rotated into overlapping relationship with the top disc and wherein a full rotation would result in said bottom disc ending up on top. In such a case the boundaries of the discs themselves could define the viewing area.

Figure 2A:
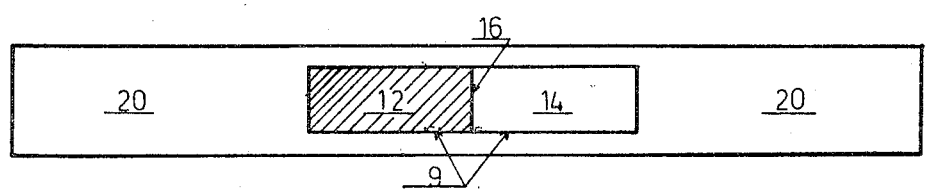
FIGS. 2A and 2B are respectively front and back perspective views of a colored means adapted for use in the device of FIG. 1.
Figure 2B:
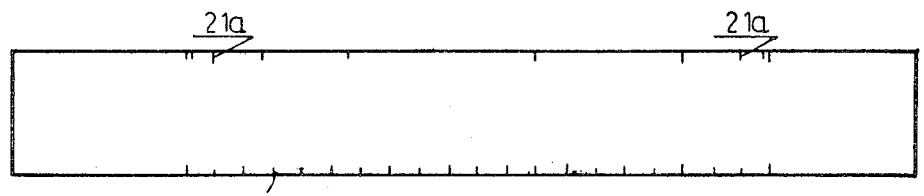

Referring to FIGS. 2A and 2B there is illustrated a front (2A) and back (2B) perspective view of colored means adapted for use with the housing 2 of FIG. 1. On the front of said means as shown there is a strip 9 having a first (12) and a second (14) colored area, said areas being contiguous and defining a boundary line 16 therebetween. Referring back to FIG. 1 said strip can alternatively have a single colored area 8 defined by a boundary line 18 with relation to a neutral background 20 wherein the coundary line of said colored area is adapted to be positioned with relation to the viewing area 6 in such a manner that all, none or part of said colored area 8 is viewable through said viewing area. For this purpose colored area 8 can be equal or only slightly larger than viewing area 6. In the colored means shown in FIG. 2 both said first colored area 12 and said second colored area 14 can each be at least equal to or slightly larger than viewing area 6 so that either said first or said second of said colors can be viewable through said viewing area to the exclusion of the other; or both can be viewable in complementary proportions. The use of one color is directed at variables which possess and are to be measured with reference to one pole e.g., confidence starts with no confidence (zero value), and ends with high confidence. The use of two colors is for bi-polar variables, e.g., like-dislike, good-bad, etc., The colors can be preselected either by the researcher or by the subject interviewed and can also optionally be interchangeable.

The measurement is done by the person who is interviewed, through his positioning of the boundary line of a colored area with reference to the limits of the viewing area. For one pole variables the limits or extremes are "no color"—signifying the lowest score to the variable, and coverage of the whole visible area by the color, signifying the highest score to the variable. For the bi-polar variable two colors can be used either independently i.e., one or two measurements "how positive" and "how negative"; or dependently where the visible area is divided into two parts, adding up to the total visible area, signifying the shares of positive and negative evaluations, in one measurement. These shares may be translated directly by the device into a continuous digital scale measuring the share(s) covered by a color(s) or directly measuring hypothesized, or experimentally pre-determined, relationship, influence, intensity, importance, or relevance of the variable to a dependent variable, e.g. probability of voting for a specific candidate.

Thus, in the device of the present invention said viewing area can be associated with a scaled reference or alternatively said colored means can be associated with a scaled reference and said scaled reference can be positioned or adapted by optical or other means so as to be visible to the interviewer but not the subject.

Thus, as illustrated in FIG. 2B the back of member 4 can be provided with a one or more scaled references 21, 21a adapted to be read against a reference point on said housing 2, in this case the outer edge or edges of slot 10. Said scaled reference can be a linear scale 21 or a non-linear scale 21a wherein the measurement thereon is direct or transformed. The scaled reference could also be on the side (not shown) of member 4 instead of the back.

Alternatively the viewing area can be associated with a scaled reference for example by providing the housing on its back, side or front with a second aperture having a scaled reference associated therewith and adapted to be read against a reference point on said member which reference point corresponds to the positioning of the boundary line 16 or 18 of said colored means with reference to said viewing area 6. Furthermore said device can be electrically or mechanically linked to a remote scaled reference and/or recording or print-out device.

As will be appreciated by those skilled in the art the devices of the present invention have many advantages over prior art measuring devices. Firstly the device of the present invention enables measurement on a continuum by most people—including young children and low education subjects whereby present methods exclude many people from measuring themselves on this type of scale. Secondly it provides for increased accuracy of measurement since it inherently is more accurate than measurement on an ordinal scale which is the type commonly used. As a practical matter it is also easier for subjects to "feel their way" and "find themselves" with the present device without the need for erasures which are time consuming and discourage corrections and reassessment. Furthermore the use of motoric and visual aspects in the measurement process reduces nonresponse by providing a more pleasant, game-like, self-measurement which stirs involvement and excitement in the measurement process leading to a more thoughtful and less boring process of self-measurement and thus adding to the accuracy in meaasurement.

It is in fact this pleasing characteristic of the device of the present invention which would tend to make it a popular and acceptable basis for educational, children's or social games and the use of the device of the present invention is such a game is included in the scope of the present invention.

Figure 3:
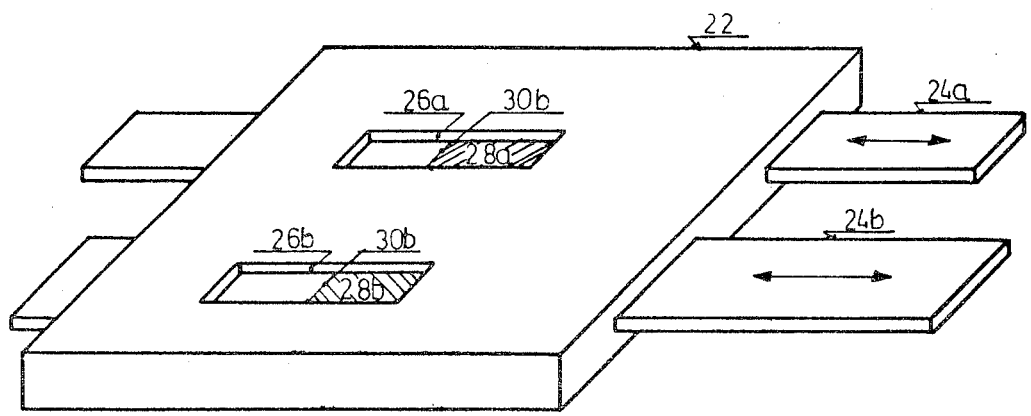
FIG. 3 is a perspective view of a modification of the device of FIG. 1.

Referring now to FIG. 3 there is illustrated a modification of the device of FIG. 1 comprising a housing 22 having two separate members 24a, 24b adapted for reciprocal sliding movement in said housing, two separate viewing areas 26a, 26b in said housing and wherein said members 24a and 24b each comprise a single colored area 28a and 28b respectively associated therewith.

This modified device is especially adapted for accurate bi-polar variable measurements by independantly measuring and cross-checking, for example, by having the subject use one colored means to indicate extent of positive want and the other colored means to indicate extent of negative "don't-want" whereby the two results are weighted and/or correlated and analyzed.

For example in polling the potential success of two parties, A and B, in an election a subject would indicate how much chance he feels party A has for success by means of positioning the boundary line 30a of colored area 28a with reference to viewing areas 26a wherein the total filling of area 26a by colored area 28a indicates 100% chance of success and the absence of any of colored area 28a in viewing area 26a indicates 0% chance of success.

Said result could be noted and then the subject would indicate by means of positioning the boundary line 30b of colored area 28b with reference to viewing area 26b how much chance he feels party B has for success.

Figure 4:
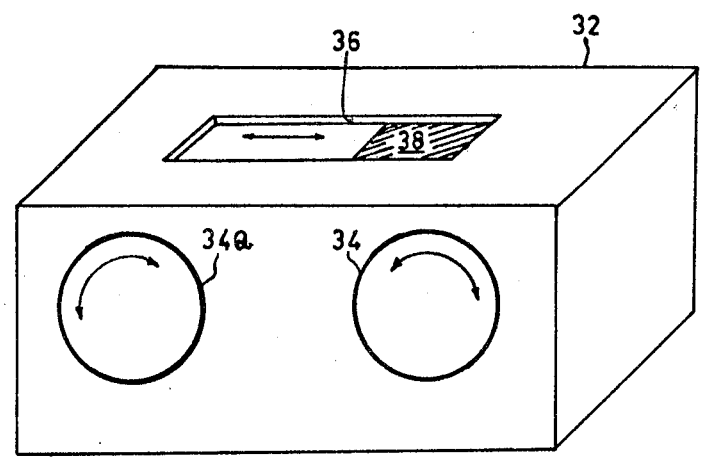
FIG. 4 is a perspective view of a different embodiment of the device of the present invention.

As hereinafter stated the present invention can be embodied in a multitude of various devices while retaining the essence of the present invention. Thus referring to FIG. 4 there is illustrated a different embodiment of the device of the present invention comprising a housing 32 having a viewing area 36 therein and colored means 38 adapted for reciprocal movement in said viewing area and two rotatable knobs 34, 34a mounted on said housing and coupled by known means (not shown) to said colored means. Thus said colored means 38 can be a tape having at least one colored section thereon and adapted to be positioned with reference to said viewing area by means of two rotatable knobs mounted on said housing to which the respective ends of said tape are attached. Alternatively there can be a single knob coupled by ratchet and pinion or worm and gear means to a strip adapted to move back and forth in said housing. Similarly said tape can be attached to a spring rewind or equivalent means.

In a preferred embodiment of said embodiment said rotatable knob or colored means is linked through said housing to a rotatable scaled reference means on the reverse side of said housing (not shown) whereby the rotation of said knob 34 or knobs 34, 34a can be immediately translated into linear or non-linear scale measurements.

Figures 5A, 5B:
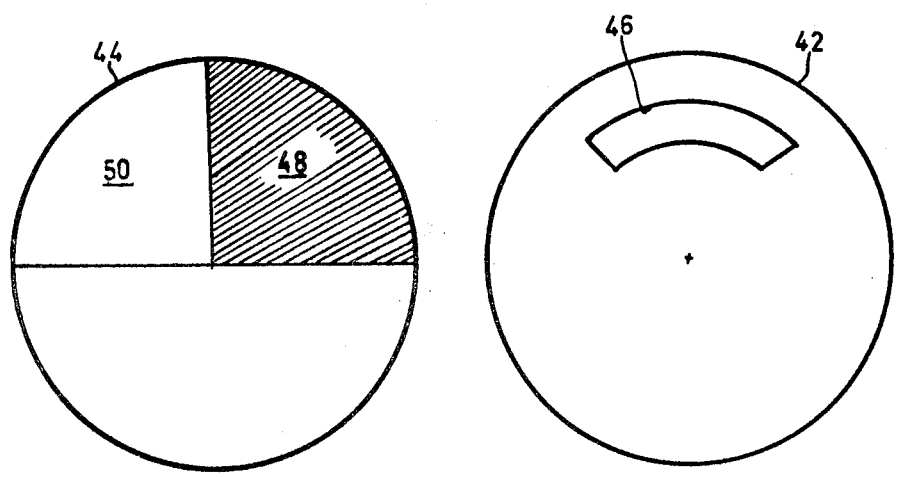
FIGS. 5A and 5B are perspective views of the componant parts of yet another embodiment of the device of the invention.

In FIGS. 5A and 5B there is shown still another, simple, embodiment of the present invention comprising a first disc 42 providing with a viewing aperture 46 and a second disc 44 providing with at least one colored area 48 wherein said discs are adapted to be concentrically mounted on a common central axis for relative reciprocal rotational movement.

In accordance with the principles discussed hereinbefore the colored means can comprise one colored area 48 or two colored areas 48 and 50. In the first instance area 50 would be a part of the neutral background of disc 44.

The devices according to the present invention can be made out of any suitable material or combination of materials including wood, plastic, metal and cardboard. Normally the device is not intended to be used within a questionnaire, but rather for use as an aid, outside a questionnaire, however, the possibility even exists of manufacturing said device of paper, for example, and incorporating a device according to the present invention after each question in a questionnaire. In such a case the device could be provided with means for affixing the relative parts after final positioning thereof so that upon return of the questionnaire the relative positioning could be noted. Similarly the colored means can be means electrically or electronically lighted or colored. Furthermore said device can be used by teachers and students to express and exemplify concepts of proportions "greater than", "smaller than", fractions and estimations of area relationships etc., for the solution of mathematical problems.

It will be evident to those skilled in the art that the invention is not limited to the details of the foregoing illustrative embodiments and that the present invention may be embodied in other specific forms without departing from the spirit or essential attributes thereof, and it is therefore desired that the present embodiments be considered in all respects as illustrative and not restrictive, reference being made to the appended claims, rather than to the foregoing description, in which it is intended to claim all modifications coming within the scope and spirit of the invention.

What is claimed is:

1. A device for measuring a subject's indication of attitude, opinion, judgment, preference, evaluation, feeling or intention when presented with a question or problem the subjective response to which is sought to be measured, the device comprising:
   (a) first means having a defined viewing area;
   (b) colored means having at least one colored area, the extent of said colored area viewable in relation to said viewing area being variable in relation to said viewing area to visually express the subjective response of the subject by selecting the extent of said colored area in said viewing area; and
   (c) means for translating the extent of said colored area viewed in said viewing area into a scaled value which corresponds to said extent of colored area, said scaled value being operatively arranged so as not to be visible to the subject when viewing said viewing area.

2. The device of claim 1, wherein said at least one colored area and said viewing area are in movable relation to one another whereby the positioning of said at least one colored area in relation to said viewing area is adapted to indicate the subjective response of the subject.

3. The device of claim 1, wherein said scaled values are positioned on the device with respect to said viewing area so as not to be visible by the subject when viewing said viewing area.

4. The device of claim 1, including manipulating means for varying the extent of said colored area viewable within said viewing area.

5. The device of claim 4, wherein the extent of said colored area viewable is varied by said manipulating means whereby the positioning of said manipulating means in relation to said colored area is adapted to indicate the subjective response of the subject.

6. The device of claim 5, wherein said manipulating means is associated with said said means for translating.

7. The device of claim 4, including a housing and wherein said at least one colored area comprises a tape having at least one colored section thereon and adapted to be positioned with reference to said viewing area by means of two rotatable knobs mounted on said housing to which respective ends of said tape are attached, said knobs constituting said manipulating means.

8. The device of claim 7, wherein said viewing area is associated with said means for translating.

9. The device of claim 1, wherein said at least one colored area is associated with said means for translating.

10. The device of claim 1, wherein said at least one colored area comprises a single colored area defined by a boundary with relation to a neutral background and wherein the boundary line of said colored area is adapted to be positioned with relation to said viewing area in such a manner that all, none or part of said colored area is viewable through said viewing area.

11. The device of claim 1, wherein said at least one colored area comprises a first and a second colored area, said colored areas being contiguous and defining a boundary line therebetween wherein said boundary line is adapted to be positioned with relation to said viewing area in such a manner that either said first, said second or both of said colored areas are viewable through said viewing area.

12. The device of claim 1, comprising two separate viewing areas and at least one respective colored area for each of said viewing areas.

13. The device of claim 1, comprising a housing, a member adapted for reciprocal sliding movement in said housing and wherein said viewing area is in said housing through which at least part of said sliding member is viewable and wherein said member comprises said at least one colored area.

14. The device of claim 13, wherein said housing is rectangular in shape having a slot cut through its central major axis and said member has a cross-section substantially the same as said slot and a length greater than said housing whereby said member is adapted for manipulation from both ends thereof.

15. The device of claim 13, wherein said member is provided with a scaled reference adapted to be read against a reference point on said housing, said scaled reference and said reference point constituting said means for translating.

16. The device of claim 13, wherein said housing is provided with a second aperture having a scaled reference associated therewith and adapted to be read against a reference point on said member which reference point corresponds to the positioning of said at least one colored area with reference to said viewing area, said scaled reference and said reference point constituting said means for translating.

17. The device of claim 1, comprising a housing having said viewing area therein, moveable colored means adapted for reciprocal movement in said viewing area and constituting said colored means having at least one colored area and at least one rotatable knob mounted on said housing and coupled to said moveable colored means.

18. The device of claim 1, comprising two concentric discs adapted for relative, reciprocal rotational movement and wherein one of said discs is provided with a viewing aperture and the other is provided with said at least one colored area.

19. A device for measuring a subject's indication of attitude, opinion, judgment, preference, evaluation, feeling or intention when presented with a question or problem the subjective response to which is sought to be measured, the device comprising:
   (a) first means having a defined viewing area;
   (b) visual means, having at least one visually distinct area, the extent of said visually distinct area viewable in relation to said viewing area being variable in relation to said viewing area to visually express the subjective response of the subject by selecting the extent of said visually distinct area in said viewing area; and
   (c) means for translating the extent of said visually distinct area viewed in said viewing area into a scaled value which corresponds to said extent of visually distinct area, said scaled value being operatively arranged so as not to be visible to the subject when viewing said viewing area.

20. The device of claim 19, wherein said scaled values are positioned on the device with respect to said viewing area so as not to be visible by the subject when viewing said viewing area.

21. The device of claim 19, including manipulating means for varying the extent of said visually distinct area viewable within said viewing area.

22. A method for measuring a subject's indication of attitude, opinion, judgment, preference, evaluation, feeling or intention when presented with a question or problem the subjective response to which is sought to be measured, the method comprising:

providing a subject with a device which includes (a) first means having a defined viewing area, (b) colored means having at least one colored area, the extent of said colored area viewable being variable in relation to said viewing area to visually express the subjective response of the subject by selecting the extent of said colored area in said viewing area, and (c) means for translating the extent of said colored area viewed in said viewing area into a scaled value which corresponds to said extent of colored area, said scaled value being operatively arranged so as not to be visible to the subject when viewing said viewing area;

presenting the subject with a question or problem the subjective response to which is sought to be measured;

moving said colored means with respect to the viewing area in said first means until the extent of said colored area viewable with relation to said viewing area indicates the subjective response to the question or problem presented to the subject, as expressed by the subject; and recording the scaled value corresponding to the extent of said colored area viewable in said viewing area by means of said means for translating, not visible to the subject.

23. A method for measuring a subject's indication of attitude, opinion, judgment, preference, evaluation, feeling or intention when presented with a question or problem the subjective response to which is sought to be measured, the method comprising:

providing a subject with a device which includes (a) first means having a defined viewing area; (b) visual means, having at least one visually distinct area, the extent of said visually distinct area viewable in relation to said viewing area being variable in relation to said viewing area to visually express the subjective response of the subject by selecting the extent of said visually distinct area in said viewing area; and (c) means for translating the extent of said visually distinct area in said viewing area into a scaled value which corresponds to said extent of visually distinct area, said scaled value being operatively arranged so as not to be visible to the subject when viewing said viewing area;

presenting the subject with a question or problem the subjective response to which is sought to be measured;

moving said visual means with respect to the viewing area in said first means until the extent of said visually distinct area viewable with relation to said viewing area indicates the subjective response to the question or problem presented to the subject, as expressed by the subject; and recording the scaled value corresponding to the extent of said visually distinct area viewable in said viewing area by means of said means for translating, not visible to the subject.

* * * * *